(12) United States Patent
Zhou

(10) Patent No.: US 11,999,933 B2
(45) Date of Patent: Jun. 4, 2024

(54) BIOLOGICAL SHEET CULTURE DEVICE AND BIOLOGICAL SHEET CULTURE FACILITY

(71) Applicant: BOE TECHNOLOGY GROUP CO., LTD., Beijing (CN)

(72) Inventor: Shi Zhou, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 220 days.

(21) Appl. No.: 16/757,403

(22) PCT Filed: Oct. 8, 2018

(86) PCT No.: PCT/CN2018/109293
§ 371 (c)(1),
(2) Date: Apr. 19, 2020

(87) PCT Pub. No.: WO2019/157826
PCT Pub. Date: Aug. 22, 2019

(65) Prior Publication Data
US 2021/0189315 A1 Jun. 24, 2021

(30) Foreign Application Priority Data
Feb. 13, 2018 (CN) .......................... 201810150478.0

(51) Int. Cl.
C12M 1/12 (2006.01)
C12M 1/00 (2006.01)
(Continued)

(52) U.S. Cl.
CPC ............ *C12M 25/14* (2013.01); *C12M 23/22* (2013.01); *C12M 23/24* (2013.01); *C12M 23/48* (2013.01); *C12M 27/18* (2013.01); *C12M 29/04* (2013.01); *C12M 29/18* (2013.01); *C12M 29/26* (2013.01); *C12M 41/14* (2013.01)

(58) Field of Classification Search
None
See application file for complete search history.

(56) References Cited

U.S. PATENT DOCUMENTS

| 4,897,359 A | * | 1/1990 | Oakley | ................. C12M 23/24 |
| | | | | 261/122.1 |
| 2002/0074470 A1 | * | 6/2002 | Ibbitson | .................... F16B 7/18 |
| | | | | 248/229.15 |

(Continued)

FOREIGN PATENT DOCUMENTS

| CN | 1894397 A | 1/2007 |
| CN | 101835886 A | 9/2010 |

(Continued)

OTHER PUBLICATIONS

Chinese Office Action and English translation corresponding to Chinese Patent Application No. 201810150478.0, dated Dec. 3, 2020 (14 pages).

*Primary Examiner* — Holly Kipouros
*Assistant Examiner* — Nathan G Esperon
(74) *Attorney, Agent, or Firm* — Myers Bigel, P.A.

(57) ABSTRACT

A biological sheet culture device includes a scaffold, a number of culture dishes for culturing biological sheets positioned on the scaffold and at least one fluid channel configured to traverse each culture dish.

18 Claims, 3 Drawing Sheets

(51) Int. Cl.
*C12M 1/04* (2006.01)
*C12M 3/00* (2006.01)

(56) References Cited

U.S. PATENT DOCUMENTS

| | | | |
|---|---|---|---|
| 2007/0148764 A1 | 6/2007 | Suzuki et al. | |
| 2008/0293132 A1* | 11/2008 | Goldman | C12M 31/04 435/292.1 |
| 2009/0029445 A1* | 1/2009 | Eckelberry | C12M 21/02 435/243 |
| 2009/0269812 A1* | 10/2009 | Sawai | C12P 19/30 435/141 |
| 2011/0104730 A1* | 5/2011 | Larsen | C12M 21/06 435/243 |
| 2013/0203106 A1* | 8/2013 | Shvets | C12M 41/40 435/375 |
| 2013/0205450 A1* | 8/2013 | Lu | C12M 23/04 435/257.1 |
| 2015/0267158 A1* | 9/2015 | McKim | C12M 21/08 435/297.5 |
| 2016/0145562 A1* | 5/2016 | Pedersen | C12M 23/38 435/297.5 |
| 2017/0037351 A1 | 2/2017 | Shimase et al. | |
| 2017/0159003 A1* | 6/2017 | Shimase | C12M 23/58 |
| 2018/0141047 A1 | 5/2018 | Ponomarenko | |

FOREIGN PATENT DOCUMENTS

| | | | | |
|---|---|---|---|---|
| CN | 105176804 | A | 12/2015 | |
| CN | 205590685 | U | 9/2016 | |
| CN | 106467892 | A | 3/2017 | |
| CN | 206843447 | | * 1/2018 | |
| CN | 206843447 | U | 1/2018 | |
| CN | 107980057 | A | 5/2018 | |
| CN | 108300661 | A | 7/2018 | |
| WO | WO-2005113742 A1 | * | 12/2005 | C12M 23/10 |

* cited by examiner

BIOLOGICAL SHEET CULTURE DEVICE AND BIOLOGICAL SHEET CULTURE FACILITY

CROSS REFERENCE TO RELATED APPLICATIONS

The present application is a 35 U.S.C. 371 national stage application of a PCT International Application No. PCT/CN2018/109293, filed on Oct. 8, 2018, which claims the benefit of a Chinese Patent Application No. 201810150478.0 filed on Feb. 13, 2018, the contents of which are incorporated herein by reference in their entireties.

TECHNICAL FIELD

The embodiment of the present disclosure relates to a biological sheet culture device and a biological sheet culture facility.

BACKGROUND

Biological sheets, such as one or more layers of plant, animal or human cell products, are obtained by subculture in culture dishes.

SUMMARY

At least one embodiment of the present disclosure provides a biological sheet culture device, comprising:
  a scaffold;
  a plurality of culture dishes for culturing biological sheets positioned on the scaffold; and
  at least one fluid channel configured to traverse each culture dish.

Optionally, at least some of the culture dishes are configured to be disposed on the scaffold at different heights.

Optionally, two adjacent culture dishes with different heights are communicated through a communication pipe, and a portion of a culture medium in a culture dish at a higher position flows into a culture dish at a lower position through the communication pipe under the state that the culture dish contains the culture medium.

Optionally, a guide plate is arranged between two adjacent culture dishes with different heights, and a portion of the culture medium in the culture dish at the higher position flows into the culture dish at the lower position through the guide plate under the state that the culture dish contains the culture medium.

Optionally, at least portions of two culture dishes communicating with at least one culture dish are located at the same side of a longitudinal direction of the at least one culture dish.

Optionally, at least portions of two culture dishes communicating with at least one culture dish are located at both sides of a longitudinal direction of the at least one culture dish.

Optionally, the above-mentioned culture device further includes a circulation pipe that connects the culture dishes of different heights and is configured to return at least a portion of a culture medium in a culture dish at a lower position to a culture dish at a higher position.

Optionally, the culture dish is also provided with an air permeable pipe, and the air permeable pipe is configured to communicate the inside of the culture dish with the outside.

Optionally, the culture device further comprises a liquid supply assembly, wherein the liquid supply assembly comprises a first pump and a liquid supply pipe connected with the first pump, and the first pump supplements culture medium into the circulation pipe through the liquid supply pipe.

Optionally, the circulation pipe is provided with a switching valve.

Optionally, the culture device further comprises a liquid discharging assembly, wherein the liquid discharging assembly comprises a water permeable pipe extending into the culture dish from the top of the culture dish and a negative pressure device positioned outside the culture dish and connected with the water permeable pipe, and the negative pressure device is configured to discharge the culture medium in the culture dish through the water permeable pipe.

Optionally, the negative pressure device is a second pump.

Optionally, a fiber film is disposed in the water permeable pipe.

Optionally, the culture dish is made of a transparent or translucent material.

Optionally, the culture device further comprises an optical detection device positioned over the culture dish and configured to monitor a culture condition of the biological sheet in the culture dish.

Optionally, the scaffold is provided with an adjusting mechanism configured to adjust the height of at least one culture dish positioned on the scaffold.

According to at least one embodiment of the present disclosure, there is provided a culture facility comprising:
  an incubator; and
  at least one culture device according to any one of the above embodiments, wherein the at least one culture device is detachably arranged in the incubator.

Additional objects and advantages of the present disclosure will be set forth in part in the detailed description which follows, and in part will be obvious from the description, or may be learned by practice of the present disclosure. The objects and advantages of the present disclosure may be realized and attained by means of the elements and combinations particularly pointed out in the appended claims.

It is to be understood that the above general description and the following detailed description are exemplary and explanatory only and are not restrictive of the claimed disclosure.

BRIEF DESCRIPTION OF THE DRAWINGS

In the drawings, which are not necessarily drawn to scale, the same reference numerals may describe similar parts in different drawings. The accompanying drawings generally illustrate various embodiments by way of example and not limitation, and together with the description and claims serve to explain the disclosed embodiments. Where appropriate, the same reference numerals are used throughout the drawings to refer to the same or similar parts. Such embodiments are illustrative and are not intended to be exhaustive or exclusive embodiments of the present device or method.

DETAILED DESCRIPTION OF THE DISCLOSURE

In order to enable those skilled in the art to better understand the technical solution of the present disclosure, the present disclosure will be described in detail below with reference to the drawings and the detailed description. Note that the terms used in this disclosure adopt the technical meaning commonly understood by those skilled in the art unless otherwise specified, but if so specified, their technical meaning shall be subject to the special description herein.

In the related art, in a device for culturing biological sheets such as cell membranes, generally, a plurality of culture dishes are placed on a scaffold individually, and a culture medium can be added to or replaced from the culture dishes one by one, which increases the complexity of operation and is not suitable for the preparation of large-scale cell membranes. In addition, the culture dish needs to be opened when adding the culture medium to the culture dish or replacing the culture medium of the culture dish, thus increasing the probability of cell contamination.

In the following embodiments, the embodiment of the present disclosure takes a cell sheet (cell membrane) as an example to explain the structure and working principle of the culture device, which is only schematic.

Figure 1:
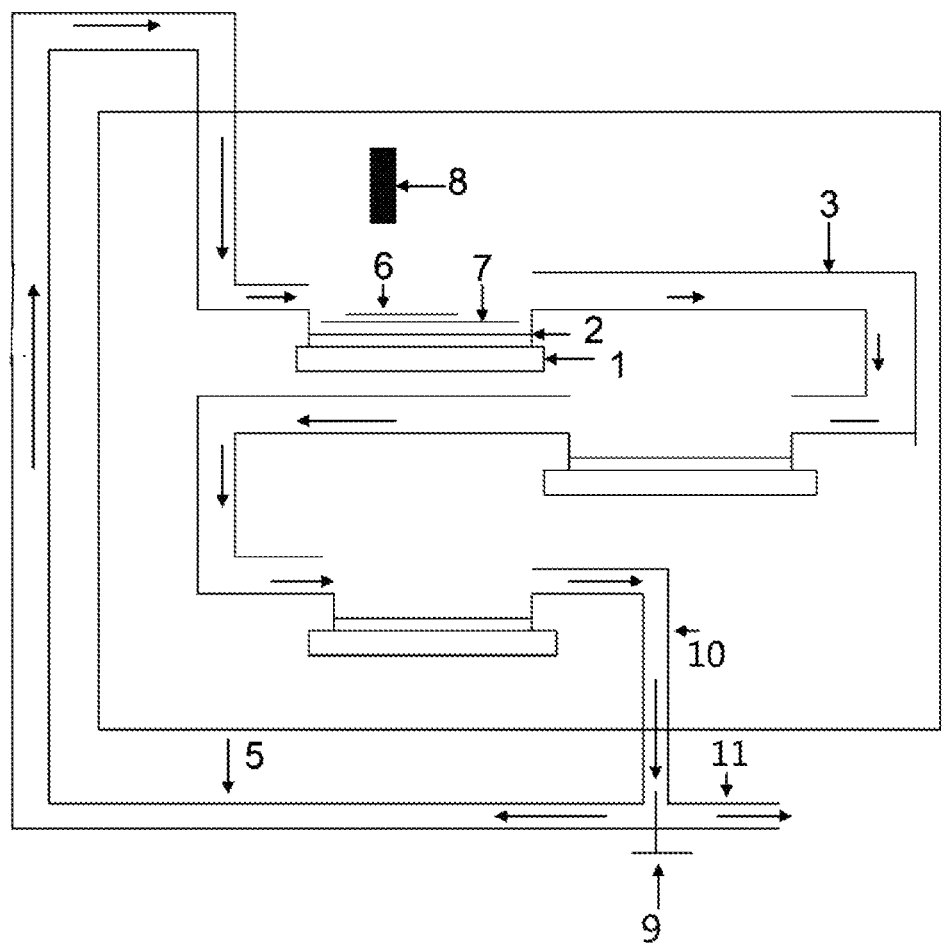
FIG. 1 is a schematic structural view of a culture device according to some embodiments of the present disclosure.
Figure 2:
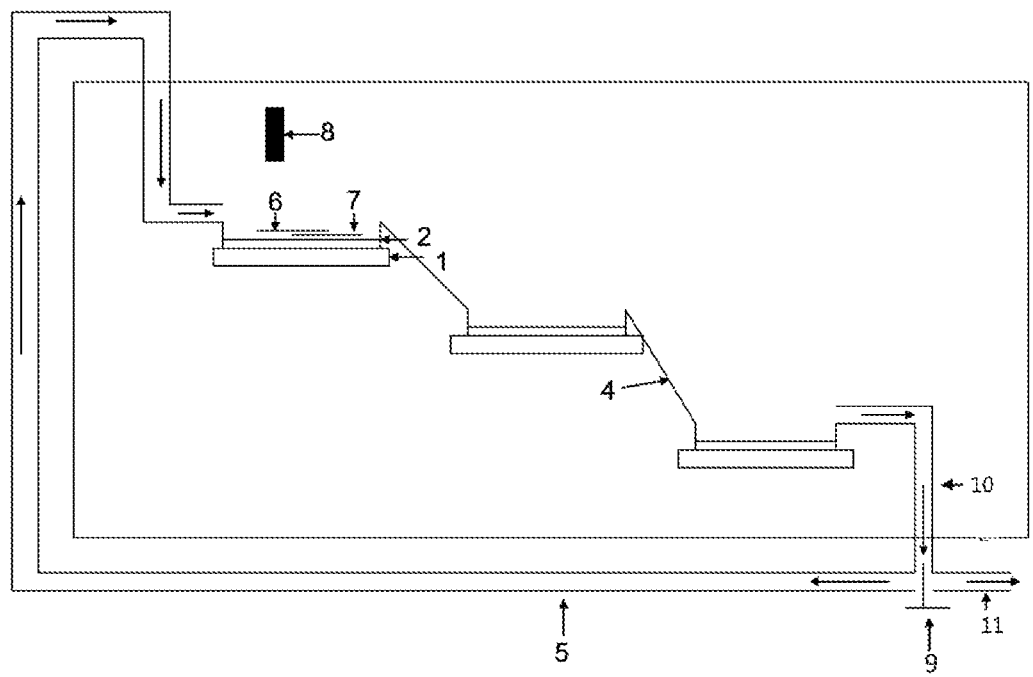
FIG. 2 is a schematic structural view of a culture device according to other embodiments of the present disclosure.
Figure 3:
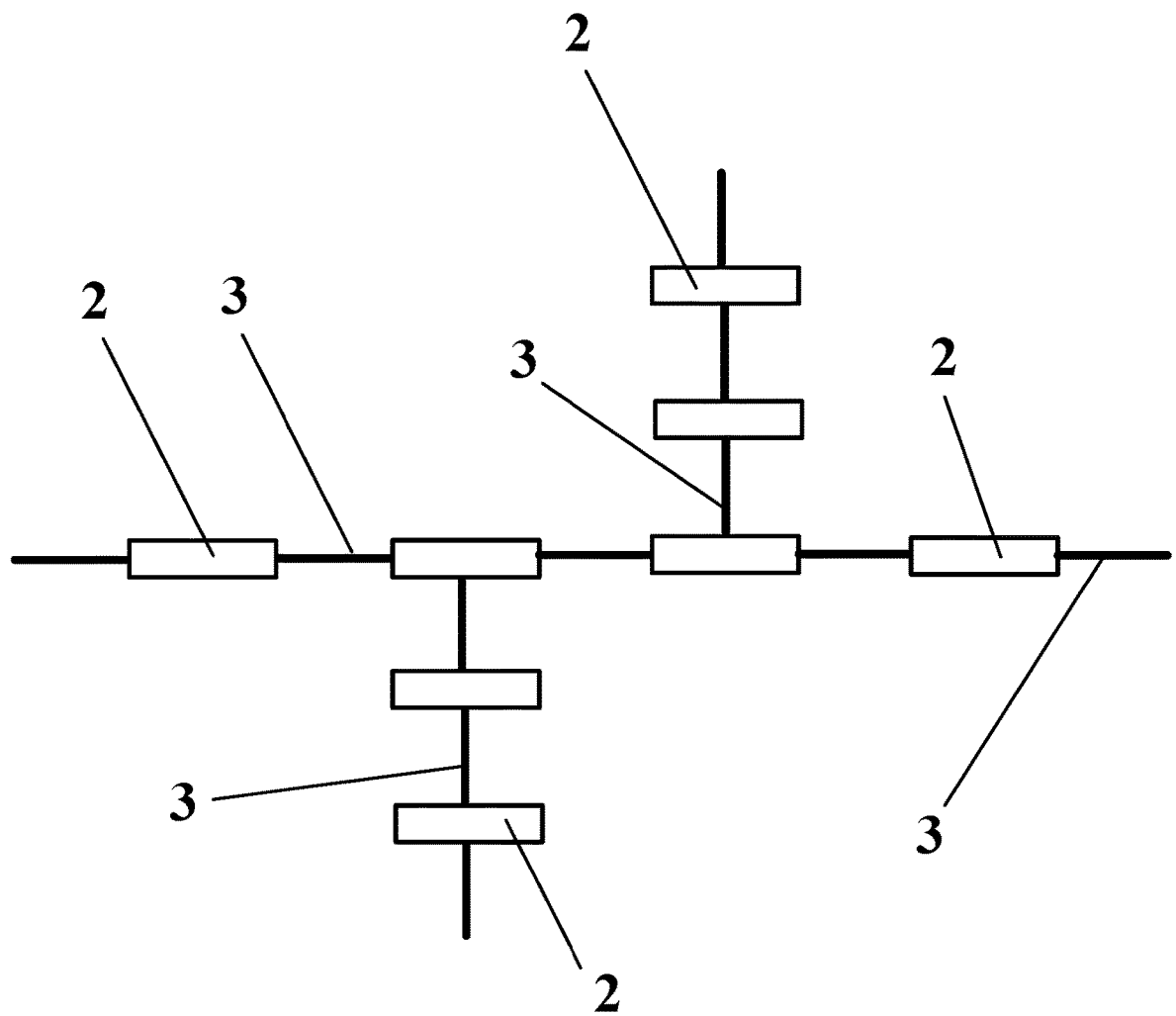
FIG. 3 is a schematic structural view of a culture device according to yet another embodiment of the present disclosure, which shows a plurality of fluid channels intersect each other through part of the plurality of culture dishes.

The embodiment of the disclosure provides a culture device which is used for preparing cell sheets, as shown in FIGS. 1 and 2. The culture device comprises a scaffold 1; a plurality of culture dishes 2 positioned on the scaffold 1, wherein the culture dishes 2 are configured to contain a culture medium to culture the cell sheets; and at least one fluid channel configured to traverse each culture dish 2.

Although FIGS. 1 and 2 show two kinds of arrangements of one fluid channel, they are by way of example only and not limitation. The at least one fluid channel may adopt other arrangements as long as the at least one fluid channel can flow through all the culture dishes 2.

For example, there may be only one fluid channel formed by connecting all the culture dishes 2 one by one in sequence.

For another example, there may be a plurality of fluid channels, each of which flows through only some of the culture dishes 2, but these fluid channels intersect each other through several culture dishes 2, so that the culture medium can also flow into all other culture dishes 2 by adding the culture medium to a suitable one of the culture dishes 2.

According to the culture device of the embodiment of the present disclosure, the culture dish 2 to be added the culture medium can be selected according to actual conditions, for example, according to the arrangement of the at least one fluid channel. For example, the culture dish 2 at the highest position in the at least one fluid channel can be selected as the suitable culture dish 2 to be added the culture medium.

In some embodiments of the present disclosure, the at least one fluid channel is configured such that by adding the culture medium to a single culture dish 2 in the at least one fluid channel, the culture medium can flow into all other culture dishes 2, i.e., into all culture dishes 2 in other fluid channels in addition to all culture dishes 2 in the at least one fluid channel. Thus, the culture medium adding operation is greatly simplified.

The culture dish 2 to be added the culture medium is not limited to a single culture dish, but may also be a plurality of culture dishes. In some embodiments of the present disclosure, the culture device is a large-scale cell sheet culture device and requires a plurality of culture dishes 2. Setting the culture dishes 2 to be added the culture medium to several, for example, two, three, etc., can still significantly facilitate the operation of adding, removing and replacing the culture medium.

In some embodiments of the present disclosure, by appropriately designing the at least one fluid channel, a single or multiple culture dishes 2 to be added the culture medium can be arranged at a position (positions) convenient for performing the adding operation.

The culture device provided in various embodiments of the present disclosure connects a plurality of culture dishes 2, so that by adding the culture medium to some (e.g., a single or several) of the culture dishes 2, the culture medium can enter all other culture dishes 2 by means of the at least one fluid channel flowing through the plurality of culture dishes 2 without opening each culture dish 2 one by one to add the culture medium or pour waste culture medium one by one. Therefore, the problem of operation complexity caused by the need of individually adding culture medium to the culture dishes 2 or replacing the culture medium of the culture dishes 2 one by one and the problem of easy pollution to the cells in the culture dishes 2 caused by opening the culture dishes 2 one by one in the related art are avoided.

Sometimes it is necessary to realize the contact between the cell sheet in each culture dish 2 and the culture medium as synchronized as possible (e.g. to ensure an equalized contact time). However, the culture dish 2 located downstream in a single fluid channel always receives the culture medium later. In view of this, in some embodiments, by arranging a plurality of fluid channels and arranging different sequences flowing through the culture dishes 2 in each fluid channel, the culture medium can enter each culture dish 2 more equally and synchronously, so that the culture conditions of the cell sheets in various culture dishes 2 are more equalized, and further the burden of monitoring the culture conditions of the membranes in real time is reduced.

For example, in some embodiments, the plurality of fluid channels may be arranged as follows: at least one of the fluid channels traverses each culture dish 2 in a first order, and the other fluid channels interconnect some of the culture dishes 2 in the at least one fluid channel in a second order different from the first order, so that the culture medium enters each culture dish 2 more equally and synchronously.

In some embodiments, the culture medium may be a fluid culture medium, such as a liquid culture medium, as long as it has fluidity.

In the embodiment of the present disclosure, the composition of the culture medium can be adjusted according to the difference of cultured cell sheets, for example, an appropriate culture medium can be selected and designed according to relevant guidance of Cold Spring Harbor (CSH) Protocols.

In the embodiment of the present disclosure, there may be various arrangements and communication modes of the plurality of culture dishes 2.

For example, a plurality of culture dishes 2 are arranged on a same horizontal plane. In this arrangement, the culture medium in the culture dishes 2 can flow between the culture dishes 2 by a driving device (e.g., a pump), and the driving device is connected to a pipeline to drive the culture medium added to the culture dishes 2 to flow along a communication direction of the culture dishes 2.

For example, a plurality of culture dishes 2 are arranged at different heights in a communication structure, and lower portions or bottom parts or other positions of the culture dishes 2 are communicated through pipelines, so that the culture medium flows between the culture dishes 2 under the action of gravity without a driving device.

For example, it is also possible that the culture medium in some of the culture dishes 2 flow under the action of the power provided by the driving device, and the culture medium of some other culture dishes 2 flow under the action of gravity.

For another example, it is also possible that the culture medium of some of the culture dishes 2 flow under both the actions of the power provided by the driving device and the gravity.

In some embodiments of the present disclosure, the scaffold 1 includes a plurality of support units configured to support the culture dishes 2; and a base configured to fix the plurality of support units.

The scaffold 1 can adopt various arrangements. For example, the fixing method of the support unit to the base includes but is not limited to at least one of screwing, clamping, bonding, etc., or alternatively the support unit and the base can be integrally molded.

In some embodiments, the scaffold 1 uses a vertical plate as the base and a horizontal plate as the support unit.

In some embodiments, the support units have identical sizes to facilitate the manufacture, storage and transportation of the entire culture device.

In some embodiments of the present disclosure, at least some of the plurality of culture dishes 2 are disposed on the scaffold 1 at different heights. For example, the support units for supporting the at least some of the culture dishes 2 may be provided at different heights, thereby realizing different height settings for the corresponding at least some of the culture dishes 2. The height referred herein refers to a distance between a bottom of the culture dish 2 (or an upper surface of the support unit supporting the culture dish 2) and a plane on which the scaffold 1 is located. As a result, the transfer of the culture medium between the culture dishes 2 in the fluid channel can be fully realized by gravity.

In some embodiments, the fluid channel may be formed by arranging connectors between adjacent culture dishes 2, and the connectors may adopt various structures.

In some embodiments, for example, as shown in FIG. 1, two adjacent culture dishes 2 with different heights are communicated with each other through a communication pipe 3, so that a portion of the culture medium in a culture dish 2 at a higher position flows into a culture dish 2 at a lower position through the communication pipe 3. In this communication mode, a front end and a rear end of the communication pipe 3 are connected with two culture dishes 2 (referred to as the front side culture dish 2 and the rear side culture dish 2 respectively). The front end of the communication pipe 3 is connected to the front side culture dish 2 to receive the culture medium therefrom, and the rear end of the communication pipe 3 is connected with the rear side culture dish 2 to feed the received culture medium into the culture dish 2 from above or horizontally. Of course, the embodiment of the present disclosure does not limit the connection position of the communication pipe 3 and the culture dish 2, and any communication mode that enables culture medium in an upper culture dish 2 to flow into a lower culture dish 2 is acceptable.

In some embodiments, for example, as shown in FIG. 2, a guide plate 4 is provided between two adjacent culture dishes 2 with different heights, so that part of the culture medium in the culture dish 2 at the higher position flows into the culture dish 2 at the lower position through the guide plate 4. In this embodiment, excess culture medium overflowed an upper port of the culture dish 2 can flow into the culture dish 2 below through the guide plate 4.

Due to different requirements on the culture device in different application scenarios, different relative arrangements can be adopted for the culture dishes 2 therein.

In some application scenarios, it is necessary to limit the size of the culture device in a horizontal plane perpendicular to the height direction, that is, it is necessary to design a culture device that extends in the height direction but is limited in the horizontal plane. To this end, in some embodiments, for example, the following relative arrangement between the culture dishes 2 may be adopted: at least portions of two culture dishes 2 communicating with at least one culture dish 2 are located at the same side of the longitudinal direction of the at least one culture dish 2. Note that, herein, the longitudinal direction of the culture dish represents an extension direction of the culture dish in a plane perpendicular to the height direction of the culture dish 2. For example, the term "longitudinal direction" may be a horizontally extending direction (i.e., a width direction of the paper surface) in the paper surface of the drawings shown in FIGS. 1 and 2, and for example, the term "longitudinal direction" may also be a direction perpendicular to the paper surface.

In some embodiments, as shown in FIG. 1, two culture dishes 2 at a left side are in communication with a culture dish 2 at a right side, and most portions of the left two culture dishes 2 are at the same side of the longitudinal direction of the right culture dish 2. In this way, the lower left culture dish 2 makes full use of a free space under the other left culture dish 2, thus making the orthographic projection of the culture device on the horizontal plane more compact.

In some embodiments, the left two culture dishes 2 and the right culture dish 2 may be overlapped in the longitudinal direction, thereby further reducing the size on the plane.

Although FIG. 1 takes three culture dishes 2 as an example, the culture device may include more culture dishes 2. The culture device including more culture dishes 2 can be realized with reference to the arrangement of the three culture dishes 2 in FIG. 1.

In some application scenarios, it is necessary to distribute the culture dishes 2 on a plane perpendicular to the height direction. With such an arrangement, some requirements can be met, such as, but not limited to, being more convenient to perform cell inoculation operations; avoiding being blocked when monitoring the culture condition of the membrane in real time; reserving a certain space under the culture dishes 2 for accommodating other devices and the like.

In some embodiments, for example, the following relative arrangement between the culture dishes 2 may be adopted: at least portions of two culture dishes 2 communicating with at least one culture dish 2 are located at both sides (i.e., at different sides) of the longitudinal direction of the culture dish 2 (see the previous special description for technical meaning).

In some embodiments, as shown in FIG. 2, three culture dishes 2 are arranged in a stepwise manner, a left culture dish 2 and a right culture dish 2 are communicated with a middle culture dish 2, and the left culture dish 2 and the right culture dish 2 are at both sides of the middle culture dish 2 in the horizontal extension direction in the paper surface.

In FIG. 2, the left culture dish 2 and the right culture dish 2 are generally shown at both sides of the middle culture dish 2 in the horizontal extension direction in the paper surface, but this is merely an example and not a limitation.

In some embodiments, adjacent culture dishes 2 in this stepped arrangement may partially overlap in the longitudinal direction.

In some cases, when adding the culture medium to a suitable culture dish 2 and eventually filling all the culture dishes 2 with the culture medium, an operator is unaware or cannot control whether a culture dish 2 at a downstream position (for example, a lower position in the case where the culture medium is flowed by gravity) is filled with the culture medium. In order to prevent the culture medium from being wasted due to overflowing of the culture medium in the culture dish 2 at the downstream position and to prevent the culture medium polluting the environment due to overflowing, in some embodiments of the present disclosure, a circulation pipe 5 is provided between a culture dish 2 at an upstream position (e.g., a higher position when the culture medium flows by gravity) and the culture dish 2 at the downstream position. In this way, after the culture dish 2 at the downstream position is filled with the culture medium, the overflowed culture medium enters the circulation pipe 5 without overflowing to the outside to cause waste and pollution. In addition, the culture medium entering the circulation pipe 5 can be returned to the culture dish 2 at the upstream position by providing a driving device, so that the culture medium overflowing at the downstream position can be recycled.

In some embodiments, the culture dish 2 at the downstream position is connected with a liquid outlet pipe 10 so as to let the culture medium flow out through the liquid outlet pipe 10, and the liquid outlet pipe 10 may communicate with the circulation pipe 5 and a discharge pipe 11 so as to return excess culture medium through the circulation pipe 5 or discharge waste culture medium or remaining culture medium through the discharge pipe 11.

Optionally, the circulation pipe 5 is provided between the culture dish 2 at the highest position and a culture dish 2 at a lowest position. In this way, after the culture dish 2 at the lowest position is filled with the culture medium, the overflowed culture medium enters the circulation pipe 5 without overflowing to the outside to cause waste and pollution. It is important that the culture medium entered the circulation pipe 5 can be returned to the culture dish 2 at the highest position by setting a driving device, so that the culture medium overflowed at the lowest position can be recycled.

Optionally, the driving device comprises a three-way valve driven by a motor (a motor driven by a power source such as electric, pneumatic or hydraulic power source can be applicable). The three-way valve has an input end and two output ends. The input end is in fluid communication with the liquid outlet pipe 10 of the culture dish 2 at the downstream position to receive overflowed culture medium therefrom, one of the two output ends is in fluid communication with the circulation pipe 5 to transfer the culture medium of the culture dish 2 to be returned to the upstream position thereto, and the other output end is in fluid communication with the outside (e.g., a drain tank) via the discharge pipe 11 to transfer the remaining culture medium so as to be discarded or recycled. The flow rate at each end of the three-way valve can be adjusted as required.

In some embodiments of the present disclosure, the culture dish 2 is enclosed, and an air permeable pipe 6 is also provided in the culture dish 2, and the air permeable pipe 6 is used for communicating the inside of the culture dish 2 with the atmosphere. The culture dish 2 is communicated with the atmosphere by the air permeable pipe, so that air required for culturing cell membranes can be ensured, and the culture medium can be prevented from being polluted by external dust, impurities and the like.

Optionally, an air permeable film, such as a thin film made of air permeable materials such as polyurethane (PU), thermoplastic polyurethane elastomer (TPU), polytetrafluoroethylene (EPTFE), etc., is provided in the air permeable pipe 6. The air permeable film can effectively prevent dust and impurities from entering the culture dish 2 through the air permeable pipe 6, and allow air required for culturing the cell membranes to enter the culture dish 2.

Since each culture dish 2 needs to consume a certain amount of culture medium for a period of time, in order to supplement the culture medium, in some embodiments of the present disclosure, the culture device further includes a liquid supply assembly (not shown), which includes a first pump and a liquid supply pipe connected to the first pump, and the first pump supplements the culture medium into the circulation pipe 5 through the liquid supply pipe. In this embodiment, the first pump is used to suck the culture medium from a container containing the culture medium, and then the culture medium is supplemented to the circulation pipe 5 through the liquid supply pipe. The supplemented culture medium enters the culture dish 2 at the upstream position through the circulation pipe 5, then the culture medium is supplemented to it, and thereafter the culture medium is accordingly supplemented to the culture dish 2 at the downstream position.

For example, the culture medium is supplemented to the circulation pipe 5 through the liquid supply pipe to enter the culture dish 2 at the most upstream position. Due to the flow of the culture medium, the culture medium in the culture dish 2 at the most upstream position to the culture medium in the culture dish 2 at the most downstream position are supplemented.

In some embodiments of the present disclosure, in order to prevent the culture medium entered the circulation pipe 5 from flowing backwards and thus entering the culture dish 2 at the downstream position first when the culture medium is supplemented by the first pump, the circulation pipe 5 is provided with a switching valve 9 which is kept closed when the first pump is operated, thereby preventing the culture medium from flowing backwards into the culture dish 2 at the downstream position. When the supplement of the culture medium is completed, the switching valve 9 can be opened.

For example, the switching valve 9 includes a solenoid valve, and the opening and closing of the solenoid valve can be controlled by an electrical signal. It is easy to understand that a mechanical valve is also applicable.

In addition, the switching valve 9 can also effectively control the connection and disconnection between each group of culture dishes 2 and the liquid level of the culture medium in each culture dish 2.

In some embodiments of the present disclosure, in order to be able to conveniently discharge the waste culture medium in the culture dish 2, the culture device further comprises a liquid discharging assembly, wherein the liquid discharging assembly comprises a water permeable pipe 7 extending into the culture dish 2 from a top of the culture dish 2 and a negative pressure device arranged outside the culture dish 2 and connected with the water permeable pipe 7. The negative pressure device draws the culture medium out of the culture dish 2 through the water permeable pipe 7. In this embodiment, the waste culture medium is discharged out of the culture dish 2 through the water permeable pipe 7 by the negative pressure device, and the discharged culture medium can be recovered in a recovery barrel.

Optionally, the negative pressure device comprises a second pump.

In some embodiments of the present disclosure, a fiber film is provided in the water permeable tube 7. The fiber film can prevent substances other than the culture medium in the culture dish 2 from being discharged out of the culture dish 2 through the water permeable pipe 7.

In some embodiments of the present disclosure, the culture dish 2 is made of transparent or translucent material to facilitate observation of the internal condition of the culture dish 2.

Optionally, transparent or translucent materials include glass, polycarbonate, low density polyethylene, polypropylene, and the like.

In some embodiments of the present disclosure, the culture device further includes an optical detection device 8, such as an optical detection device based on an imaging element such as CCD or CMOS or infrared imaging element, and the optical detection device 8 is disposed over the culture dish 2 for monitoring the culture condition of the cell sheet in the culture dish 2.

Optionally, the culture state of the cell sheet includes at least one of shape, area, thickness, uniformity, flatness, distribution density, survival rate, etc.

In some embodiments of the present disclosure, the scaffold 1 is provided with an adjusting mechanism configured to adjust the height of at least one of the culture dishes 2 located on the scaffold 1. As an example of multi-support unit-base structure of the scaffold 1 already described above, optionally, an adjusting structure may be provided on the base so as to realize synchronous height adjustment of each support unit fixed on the base through adjustment of the adjusting structure. When rigid connection is adopted between the culture dishes 2, for example, the guide plate 4, when the height adjustment of the support units is not synchronized, the connection with the guide plate 4 will be affected or even destroyed. Through the synchronous height adjustment of each support unit, a stable connection relationship between each culture dish 2 and the guide plate 4 can be ensured. Optionally, when a non-rigid connection is used between the culture dishes 2, for example, a flexible communication pipe 3, an adjusting mechanism may be independently provided for at least some of the support units, for example, for each support unit, so as to more flexibly adjust the height of each culture dish 2.

For example, the adjusting mechanism may have various types or structures. For example, the adjusting mechanism may be a nut and screw pair structure, or a pneumatic, hydraulic, electric or other driving mechanism. The embodiments of the present disclosure do not limit the type or structure of the adjusting mechanism.

The culture device provided by various embodiments of the present disclosure can be used for preparing various biological sheets such as cell sheets.

In some embodiments, the culture dish 2 is detachable and removable with respect to the scaffold 1. When the culture dish 2 is disposed in place on the scaffold 1, at least one fluid channel capable of traversing each culture dish 2 is formed.

For example, the biological sheets can be cultured and formed using the culture device based on the following methods, taking the cell sheets as an example:

Step S10: disposing inoculated culture dishes 2 in place on a scaffold 1, Step S20: supplying a culture medium to the most upstream culture dish 2 (or a plurality of culture dishes 2 selected to be added the culture medium) through a liquid supply pipe, and guiding excess culture medium in the culture dish 2 at the upstream position into a culture dish 2 at a downstream position through at least one fluid channel, so that all the culture dishes 2 are filled with culture medium;

Step S30: communicating the interior of the culture dish 2 and the atmosphere via an air permeable pipe 6 at the top of the culture dish 2 so as to provide an environment required for growth and reproduction;

Step S40: detecting the culture condition of the cells in the culture medium using an optical detection device 8. If it is detected that the cells in the culture dish 2 have grown into a qualified cell sheet, the culture is ended. Excess culture medium can be discharged through the discharge pipe 11.

In step S10, the inoculation operation may be directly performed in a state where the culture dishes 2 have been placed on the scaffold 1. Under the condition that the culture dish 2 is detachable and removable with respect to the scaffold 1, the cell sheet in the culture dish 2 can also be inoculated externally first, for example, by using a commonly used well plate, and then the inoculated culture dishes 2 are disposed on the scaffold 1 in place, so that the operation is flexible and convenient.

In some embodiments of the present disclosure, there is also provided a culture facility including:

an incubator; and at least one culture device described in each of the above embodiments, wherein the at least one culture device is detachably disposed in the incubator.

In this way, the user can add or remove culture devices in the incubator as required, and can also arrange a plurality of culture devices in different mutual arrangements in the incubator as required. Once a certain culture device is damaged, the culture device can be replaced without replacing other culture devices together, so that the maintenance work of the whole culture facility is more flexible and the cost is lower.

The above specific embodiment has been explained with a cell sheet as a culture object, but it should be understood that the culture object of the culture device and the culture facility according to the embodiment of the present disclosure is not limited to the cell sheet, but covers all biological sheets having a three-dimensional structure such as physiological slices, skin samples, plant tissues, and the like, for example, the biological sheets may be cell sheets.

It should be noted that the present disclosure uses expressions "one embodiment", "an embodiment" or "some embodiments" along with their derivatives, and these expressions and terms mean that a specific feature, structure or characteristic described in connection with the embodiment is included in at least one embodiment. The appearances of the phrase "in one embodiment" in various places in this disclosure are not necessarily all referring to the same embodiment.

It should be understood that the words "a" or "an" in the claims of the present disclosure do not exclude plural numbers, and are only intended for convenience of description and should not be construed as limiting the scope of protection of the present disclosure.

In addition, although exemplary embodiments have been described herein, the scope thereof includes any and all embodiments based on the present disclosure having equivalent elements, modifications, omissions, combinations (e.g., solutions where various embodiments are incorporated by reference), adaptations, or variations. Elements in the claims are to be interpreted broadly based on the language employed in the claims, and are not limited to the examples described in this specification or during the implementation of this application, and examples thereof are to be interpreted as non-exclusive. Therefore, the specification and examples are intended to be considered as examples only, with the true scope and spirit being indicated by the following claims and the full scope of equivalents thereof.

The above description is intended to be illustrative rather than limiting. For example, the above examples (or one or more solutions thereof) may be used in combination with each other. For example, one of ordinary skill in the art can use other embodiments when reading the above description. In addition, in the above-described embodiments, various features may be grouped together to simplify the present disclosure. This should not be interpreted as an intention that an unclaimed disclosed feature is essential to any claim. On the contrary, the subject matter of the present disclosure may be less than all features of a particular disclosed embodiment. Thus, the following claims are hereby incorporated into the specific embodiments as examples or embodiments, wherein each claim is independently taken as a separate embodiment, and it is contemplated that these embodiments may be combined with each other in various combinations or permutations. The scope of the present disclosure should be determined with reference to the appended claims and the full scope of equivalents to which such claims are entitled.

The invention claimed is:

1. A biological sheet culture device comprising:
a scaffold;
a plurality of culture dishes for culturing biological sheets on the scaffold; and
a plurality of communication pipes, each of which is configured to fluidly communicate with two adjacent culture dishes;
wherein the plurality of culture dishes and the plurality of communication pipes are configured to form a plurality of fluid channels that are continuous, each fluid channel is configured to traverse every culture dish of the plurality of culture dishes, a sequence of one fluid channel of the plurality of fluid channels flowing through the plurality of culture dishes is different from that of at least one other fluid channel of the plurality of fluid channels flowing through the plurality of culture dishes wherein the plurality of fluid channels intersect each other through part of the plurality of culture dishes,
wherein the plurality of fluid channels are configured such that adding culture medium to any single culture dish of the plurality of fluid channels can cause the culture medium to flow into all other culture dishes of the plurality of fluid channels,
wherein an air permeable pipe is provided in a culture dish of the plurality of culture dishes, the air permeable pipe is configured to communicate from inside of the culture dish to outside of the culture dish, a permeable film is provided in the permeable pipe and configured to prevent dust and impurities from entering the culture dish through the air permeable pipe and allow air to enter the culture dish, and
wherein the biological sheet culture device further comprises a water permeable pipe that extends into a culture dish of the plurality of culture dishes from a top of the culture dish of the plurality of culture dishes, and a fiber film is provided in the water permeable pipe and configured to prevent substances other than the culture medium in the culture dish from being discharged out of the culture dish through the water permeable pipe.

2. The biological sheet culture device according to claim 1, wherein at least two of the culture dishes are configured to be on the scaffold at different heights.

3. The biological sheet culture device according to claim 2, wherein two adjacent culture dishes with different heights are configured to be communicated through a communication pipe, and
wherein a portion of a culture medium in a culture dish at a higher position of the two adjacent culture dishes is configured to flow into a culture dish at a lower position of the two adjacent culture dishes through the communication pipe under a state that the culture dish at the higher position includes the culture medium.

4. The biological sheet culture device according to claim 3, wherein at least portions of two culture dishes communicating with at least one culture dish are at a same side of a longitudinal direction of the at least one culture dish.

5. The biological sheet culture device according to claim 3, wherein at least portions of two culture dishes communicating with at least one culture dish are at both sides of a longitudinal direction of the at least one culture dish.

6. The biological sheet culture device according to claim 3, further comprising:
a circulation pipe connected to culture dishes of different heights and configured to return at least part of a culture medium in a culture dish at a lower position into a culture dish at a higher position.

7. The biological sheet culture device according to claim 2,
wherein a guide plate is between two adjacent culture dishes with different heights, and
wherein a portion of a culture medium in a culture dish at a higher position of the two adjacent culture dishes is configured to flow into a culture dish at a lower position of the two adjacent culture dishes through the guide plate under a state that the culture dish at the higher position includes the culture medium.

8. The biological sheet culture device according to claim 7, wherein at least portions of two culture dishes communicating with at least one culture dish are at a same side of a longitudinal direction of the at least one culture dish.

9. The biological sheet culture device according to claim 7, wherein at least portions of two culture dishes communicating with at least one culture dish are at both sides of a longitudinal direction of the at least one culture dish.

10. The biological sheet culture device according to claim 2, further comprising:
a circulation pipe connected to culture dishes of different heights and configured to return at least part of a culture medium in a culture dish at a lower position into a culture dishes at a higher position.

11. The biological sheet culture device according to claim 10, further comprising:
a liquid supply assembly,
wherein the liquid supply assembly comprises a first pump and a liquid supply pipe connected with the first pump, and
wherein the first pump supplements the culture medium into the circulation pipe through the liquid supply pipe.

12. The biological sheet culture device according to claim 10, wherein the circulation pipe is associated with a switching valve.

13. The biological sheet culture device according to claim 1, further comprising:
a liquid discharging assembly,
wherein the liquid discharging assembly comprises the water permeable pipe that extends into the culture dish of the plurality of culture dishes from the top of the culture dish of the plurality of culture dishes and a negative pressure device outside the culture dish of the plurality of culture dishes and connected with the water permeable pipe, and
wherein the negative pressure device is configured to discharge a culture medium out of the culture dish of the plurality of culture dishes through the water permeable pipe.

14. The biological sheet culture device according to claim 13, wherein the negative pressure device comprises a second pump.

15. The biological sheet culture device according to claim 1, wherein at least one culture dish of the plurality of culture dishes comprises a transparent material or a translucent material.

16. The biological sheet culture device according to claim 1, further comprising:
an optical detection device over at least one culture dish of the plurality of culture dishes and configured to monitor a culture condition of at least one of the biological sheets in the at least one culture dish.

17. The biological sheet culture device according to claim 1, wherein the scaffold is associated with a culture dish height adjustor configured to adjust a height of at least one culture dish on the scaffold.

18. A biological sheet culture facility comprising:
an incubator; and
at least one biological sheet culture,
wherein the at least one biological sheet culture is detachable from the incubator,
wherein each biological sheet culture device comprises:
a scaffold;
a plurality of culture dishes for culturing biological sheets positioned on the scaffold; and
a plurality of communication pipes, each of which is configured to fluidly communicate with two adjacent culture dishes;
wherein the plurality of culture dishes and the plurality of communication pipes are configured to form a plurality of fluid channels that are continuous, each fluid channel is configured to traverse every culture dish of the plurality of culture dishes, a sequence of one fluid channel of the plurality of fluid channels flowing through the plurality of culture dishes is different from that of at least one other fluid channel of the plurality of fluid channels flowing through the plurality of culture dishes wherein the plurality of fluid channels intersect each other through part of the plurality of culture dishes,
wherein the plurality of fluid channels are configured such that adding culture medium to any single culture dish of the plurality of fluid channels can cause the culture medium to flow into all other culture dishes of the plurality of fluid channels,
wherein an air permeable pipe is provided in a culture dish of the plurality of culture dishes, the air permeable pipe is configured to communicate from inside of the culture dish to outside of the culture dish, a permeable film is provided in the permeable pipe and configured to prevent dust and impurities from entering the culture dish through the air permeable pipe and allow air to enter the culture dish, and
wherein the biological sheet culture device further comprises a water permeable pipe that extends into a culture dish of the plurality of culture dishes from a top of the culture dish of the plurality of culture dishes, and a fiber film is provided in the water permeable pipe and configured to prevent substances other than the culture medium in the culture dish from being discharged out of the culture dish through the water permeable pipe.

* * * * *